US008552221B2

(12) United States Patent
Braun et al.

(10) Patent No.: US 8,552,221 B2
(45) Date of Patent: Oct. 8, 2013

(54) PROCESS FOR THE MANUFACTURE OF HALOGENATED PRECURSORS OF ALKENONES UNDER SPECIFIC CONDITIONS

(75) Inventors: Max Josef Braun, Wedemark (DE); Stefan Palsherm, Barsinghausen (DE); Uta Claassen, Hohenhameln (DE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 12/999,730

(22) PCT Filed: Jul. 5, 2010

(86) PCT No.: PCT/EP2010/059549
§ 371 (c)(1), (2), (4) Date: May 23, 2011

(87) PCT Pub. No.: WO2011/003856
PCT Pub. Date: Jan. 13, 2011

(65) Prior Publication Data
US 2012/0101305 A1    Apr. 26, 2012

Related U.S. Application Data

(63) Continuation-in-part of application No. PCT/EP2009/058525, filed on Jul. 6, 2009.

(30) Foreign Application Priority Data

Jan. 7, 2010   (EP) .................................... 10150229

(51) Int. Cl.
*C07C 45/65*   (2006.01)
(52) U.S. Cl.
USPC ......................................... 568/392; 568/404
(58) Field of Classification Search
USPC ................................................ 568/392, 404
See application file for complete search history.

(56) References Cited

U.S. PATENT DOCUMENTS

| 5,708,175 | A | 1/1998 | Koyanagi et al. |
| 6,428,199 | B1 | 8/2002 | Rupaner et al. |
| 7,057,079 | B2 | 6/2006 | Braun et al. |
| 7,405,328 | B2 | 7/2008 | Hausmann et al. |
| 2006/0198771 | A1 | 9/2006 | Devic |

FOREIGN PATENT DOCUMENTS

| EP | 0744400 A2 | 11/1996 |
| WO | WO 03066558 A2 | 8/2003 |
| WO | WO 20040108647 A2 | 12/2004 |
| WO | WO 20090006217 A1 | 1/2009 |
| WO | WO 20100000871 A2 | 1/2010 |
| WO | WO 20100037688 A1 | 4/2010 |
| WO | WO 20110003854 A1 | 1/2011 |
| WO | WO 20110003860 A1 | 1/2011 |

OTHER PUBLICATIONS

U.S. Appl. No. 12/999,673, filed Dec. 17, 2010, Max Braun, et al.
U.S. Appl. No. 13/120,505, filed Mar. 23, 2011, Max Braun.
U.S. Appl. No. 12/999,714, filed Mar. 31, 2011, Max Braun, et al.
U.S. Appl. No. 12/999,750, filed Apr. 7, 2011, Max Braun, et al.
Tietze, L. F., et al—"Synthesis of Alkyl Propanoates by a Haloform Reaction of a Trichloro Ketone: Preparation of ethyl 3,3-Diethoxypropanoate"; Organic Syntheses, 1990, vol. 69, pp. 238-244, XP 008037891; 7 pgs.
Tietze, L.-F., et al—"Highly Efficient Syntheses of Alkyl 3,3-Dialkoxypropanoates, Alkyl 4-Ethoxy-2-oxo-3-butenoates, and Monoprotected Malonaldehydes", Synthesis, 1988, No. 4, pp. 274-277; XP-002587967; 4 pgs.

*Primary Examiner* — Sikarl Witherspoon
(74) *Attorney, Agent, or Firm* — Beatrice C. Ortego

(57) ABSTRACT

A process for preparing a halogenated precursor of an alkenone, which comprises reacting a carboxylic acid halide with a vinyl ether in a liquid reaction medium under turbulent conditions and a process for preparing an alkenone, by eliminating hydrogen halide from said precursor to form the alkenone.

19 Claims, No Drawings

PROCESS FOR THE MANUFACTURE OF HALOGENATED PRECURSORS OF ALKENONES UNDER SPECIFIC CONDITIONS

CROSS-REFERENCE TO RELATED APPLICATIONS

This application is a U.S. national stage application under 35 U.S.C. §371 of International Application No. PCT/EP2010/059549 filed on Jul. 5, 2010, which claims priority under 35 U.S.C. §119(a)-(d) or (f), §365(b) or §365(a) to International Application No. PCT/EP2009/058525 filed on Jul. 6, 2009 and to European Application No. EP-10150229.2 filed on Jan. 7, 2010, said International Application PCT/EP2010/059549 being a continuation-in-part application under 35 U.S.C. §365(c) of International Application No. PCT/EP2009/058525 designating the United States filed on Jul. 6, 2009, the whole content of each of these applications being incorporated herein by reference for all purposes.

Halogenated alkenones, such as 4-ethoxy-1,1,1-trifluoro-3-butenone (ETFBO), are building blocks in chemical synthesis, as disclosed, for example, in U.S. Pat. No. 5,708,175. They may be prepared by reacting an acid chloride with a vinyl ether in the presence of a base, as described in the aforementioned U.S. patent. For this reaction, the base may also be used in excess as a solvent.

WO 03/066558 discloses production of alkenones from vinyl ethers and acid halides or acid anhydrides in the presence of onium salts. In the case of trifluoroacetic anhydride addition to ethyl vinyl ether, both addition of ethyl vinyl ether to a reaction medium containing trifluoroacetic anhydride and addition of trifluoroacetic anhydride to a reaction medium containing ethyl vinyl ether are described.

WO 2004/108647 discloses i.a. simplified production of alkenones comprising addition of carboxylic acid halides to vinyl ethers. In the examples, trifluoroacetyl chloride is added to ethyl vinyl ether.

It is an object of the present invention to provide an improved process for the preparation of halogenated precursors of alkenones. It is another object of the present invention to provide a process for the manufacture of alkenones from the halogenated precursors, in particular concerning the selectivity and the yield of the production, whereby, amongst others, separation of the product can be simplified and loss of material and need for disposal of by-products can be reduced.

The invention relates to a process for preparing a halogenated precursor of an alkenone, which comprises reacting a carboxylic acid halide with a vinyl ether in a liquid reaction medium, wherein the reaction medium is in turbulent state.

The process is preferably performed to prepare a halogenated alkenone precursor of formula (I)

$$R^1—C(O)—CH_2—CHX—OR^2 \quad (I)$$

wherein $R^1$ represents a C1-C10 alkyl group which is optionally substituted by at least one halogen atom or $R^1$ represents $CF_3$, $CF_2Cl$, $CF_2H$; and $R^2$ represents aryl, substituted aryl, or a C1-C10 alkyl group which is optionally substituted by at least one halogen atom and X represents fluorine, chlorine or bromine wherein an acid halide corresponding to Formula (II): $R^1—C(O)X$ (II) in which X represents fluorine, chlorine or bromine and $R^1$ has the meaning given above, is reacted with a vinyl ether corresponding to Formula (III): $CH_2=C(H)—OR^2$ (III) in which $R^2$ has the meaning given above.

$R^1$ is often a fluorinated C1-C4 alkyl group. $R^1$ preferably represents methyl, ethyl, n-propyl, isopropyl or methyl, ethyl, n-propyl or isopropyl substituted by at least one fluorine atom. It is especially preferred if $R^1$ represents methyl, ethyl or methyl or ethyl substituted by at least one fluorine atom. $CF_3$, $CF_2H$, $CF_2Cl$, $C_2F_5$, $C_3F_7$ are particularly preferred as $R^1$. $CF_3$, $CF_2Cl$ and $CF_2H$ are more particularly preferred as $R^1$.

$R^2$ can be selected for example from aryl, for example, phenyl, C1-C4 alkyl groups and/or phenyl substituted by halogen atoms. $R^2$ is often a C1-C4 alkyl group. Preferably, $R^2$ represents a linear or branched C1-C4 alkyl group, and particularly preferably $R^2$ represents methyl, ethyl, n-propyl or isopropyl, most preferably a methyl or an ethyl group.

X is preferably selected from fluorine and chlorine, more preferably X is chlorine.

The alkenones which can be prepared from the halogenated alkenone precursors of formula (I) are the alkenones of formula (IV), $$R^1—C(O)—CH=CH—OR^2 \quad (IV)$$

$R^1$ and $R^2$ have the same meaning as in formula (I).

The term "turbulent" state includes the meaning used in fluid dynamics, indicating i.a. high momentum convection and high Reynolds numbers, as distinguished from a "laminar" state; but the term is not limited to this meaning. The term "turbulent" broadly denotes a very efficient mixing of the reaction mixture.

The turbulent state of the reaction medium can be achieved, for example, by an operation selected from stirring, passing the reaction medium through a flow resistance, mixing the reaction medium through introduction of gas bubbles such as for example inert gas bubbles. In another aspect, the reaction is carried out under conditions of pressure and temperature under which at least one of the starting materials is gaseous. In that case, it is advantageous to introduce the starting material in liquid form. Gas bubbles are generated which provide turbulency in the reaction medium when the liquefied starting material gets into the gaseous state. Further, the vaporization consumes heat from the reaction medium what is also very advantageous. Carboxylic acid halide, in particular trifluoroacetyl chloride is suitable starting material for this purpose.

Accordingly, one aspect of the present invention concerns a process for the manufacture of a halogenated precursor of an alkenone which comprises reacting a carboxylic acid halide with a vinyl ether in a liquid reaction medium, wherein at least a part of the carboxylic acid halide is introduced into the reaction medium in liquid state. Preferably, at least 99% by weight of the acyl halide is introduced into the reaction medium in liquid state.

The preferred starting material of this process corresponds to the preferred starting material of the process described above. An acyl chloride of formula $R^1—C(O)X$ is preferred wherein $R^1$ is $CF_3$, $CF_2H$, $CF_2Cl$, $C_2F_5$, $C_3F_7$. A vinyl ether of formula $CH_2=C(H)—OR^2$ is preferred wherein $R^2$ represents methyl, ethyl, n-propyl or isopropyl. The preferred precursor is CETFBO.

The stirring in the reaction medium may be realized by means of internal stirring such as a turbine or an agitator, or by means of a recirculation pipe exterior to the reactor.

Typical examples of a flow resistance are for example shaped bodies which can be placed in a reactor such as glass rings and Raschig rings.

In a particular aspect of this specific embodiment, which is particularly advantageous when the process is carried out in continuous mode, the vinyl ether and the carboxylic acid halide may be introduced into the liquid reaction medium through a concentric nozzle having an internal supply tube and an external supply tube. In this aspect, the vinyl ether is preferably supplied through the internal supply tube and the carboxylic acid halide is preferably supplied through the external supply tube.

It has been found, surprisingly, that by creating a turbulent state in the liquid reaction medium, hot spots can be substantially avoided in said reaction medium, thereby improving the yield and purity of the halogenated precursor of the alkenone and of the alkenone obtained from the precursor.

For the purpose of the present invention, the term "hot spot" denotes in particular a zone of the reaction medium having a substantially higher temperature than the temperature at which the reaction is carried out. "Substantially higher temperature" is understood a temperature which is at least 5° C., often at least 10° C. higher than the average temperature of the liquid reaction medium.

It was observed that hot spots cause the elimination of hydrogen halide, and hydrogen halide was found to cause undesired side reactions. Thus, according to the invention, it is preferred to provide a very low level of hydrogen halide formation in the addition reaction, preferably to substantially avoid its formation at all. "Substantially avoid" denotes in particular maintaining a content of hydrogen halide in the reaction medium of equal to or lower than 1% wt. Preferably, this content is maintained equal to or lower than 0.5% wt. When the formation of hydrogen halide is substantially avoided, a content of hydrogen halide in the reaction medium equal to or higher than 0.01% wt albeit equal to or higher than 0.1% wt relative to the total weight of the reaction medium is acceptable.

The process according to this specific embodiment, generally comprises carrying out the reaction at a temperature from 0° C. to 40° C., preferably from 10° C. to 30° C., more preferably at equal to or about 25° C. and most preferably at equal to or about 20° C. If desired, the reaction can also be performed at temperatures below 0° C.; e.g., between 0° C. and −50° C., but the reaction rate is lower. It is preferred to operate at a temperature from 0° C. to 40° C.

In the process according to this specific embodiment, the reaction is preferably carried out in a continuously stirred tank reactor (CSTR).

In a particular aspect said the continuously stirred tank reactor is combined with a plug flow reactor. In that case, generally, at least a part of the liquid reaction medium is withdrawn from the continuously stirred tank reactor and subjected to further reaction in a plug flow reactor. In this case, the CSTR reactor is usually in the turbulent state while the plug-flow reactor can be in turbulent or laminar flow state. In a plug-flow reactor, it is preferred to perform the reaction in a laminar flow state if the acyl halide is reacted with the vinyl ether in a molar ratio of acyl halide:vinyl ether of 1:1 or lower than 1:1 (i.e., in the presence of equimolar amounts or with an excess of the vinyl ether). If the plug flow reactor is operated in a turbulent state, it is preferred to apply an excess of the acyl halide because the gas bubbles of it intensify the mixing of the components of the reaction medium.

Particular embodiments of CSTR include reactors which consist of one or more cylindrical or spherical tanks wherein the turbulent state of the liquid reaction medium is created by any of the means described above. When more than one CSTR reactor is used, for example 2, 3 or 4 reactors, it is advantageous to split the feed of vinyl ether so as to feed vinyl ether to each reactor.

Particular embodiments of plug flow reactor are in the form of a cylindrical tube through which the feed enters at one end and exits at the other end.

The addition reaction of the acid halide and the vinyl ether is exothermic. As mentioned above, it is preferably performed at a temperature from 0° C. to 40° C., and thus, the reaction medium is preferably cooled.

In another particular aspect said the continuously stirred tank reactor is combined with a heat exchanger. Said heat exchanger advantageously can remove heat from the reactor during the exothermic reaction. The heat exchanger can be a separated device added to the CSTR or the heat exchanger and the reactor can be combined into a single piece of equipment.

By way of illustration, the following devices can be used as heat exchangers, especially when added to the CSTR: double jacket, external and internal coils etc.

If the heat exchanger is a device separated from the reactor, a part of the reaction medium can be passed through a loop via a heat exchanger or a cooling machine. This is preferably performed continuously.

The stirrers may be single-stage or multistage embodiments, especially those which produce not only a tangential flow component but also an axial flow field. Preferred stirrers are those having 1 to 7 stirring blade stages attached, preferably equidistantly, on the axial stirrer shaft. Examples are blade, anchor, impeller, Pfaudler, disk, helical, bar, finger propeller, sigma, paddle, pitched-blade and coaxial stirrers, such as cross-arm. Multiflow, multipulse countercurrent, Intermig and Interpro stirrers. A suitable reactor is described in U.S. Pat. No. 6,428,199. The reactor described therein has a stirring mechanism, incoming and outgoing lines and a removable head wherein both the incoming and outgoing lines and the stirring mechanism are installed on the reactor floor.

A reactor which can be used in the process of the present invention is described in US patent application publication 2006/0198771 A1. A cylindrical vertical stirred reactor provided with means of injection of gaseous (or liquid) reactants at the bottom, and, as essential parts, centrifugal turbines arranged along a single vertical agitating shaft. The shaft is driven by a geared motor unit which is most often situated either above or below the reactor. The reactor may be equipped with counterbaffles and/or a heat exchanger.

Another apparatus which can be used for preparing halogenated precursors of an alkenones is now described.

The apparatus comprises two means, wherein the first means comprises a circulation system with a boiler, pipes filled with Raschig rings, centrifugal pump, tubular reactors each with a pipe. Product can be added or removed (for analysis purposes) before and after each of these reactors. For safety reasons, a further length of pipe with cooler and cold traps can be mounted after circulation; wherein the second means is used as a receiver and for the thermolysis of the organic product precursors to the organic products, for example, from 4-chloro-4-ethoxy-1,1,1-trifluoro-butan-2-one (CETFBO) to ETFBO and comprises ceramic boiler with column pipes with Raschig rings and cooler with take-off.

Reactors which are coated with a ceramic at least on the inner walls are especially suitable because ceramic was found to be very resistant under the aggressive conditions of the process of the invention. Accordingly, another aspect of the present invention concerns a process for the manufacture of a halogenated precursor of an alkenone which comprises reacting a carboxylic acid halide with a vinyl ether in a liquid reaction medium, wherein the reaction is performed in a reactor the inner walls of which are coated with a ceramic. If desired, the reactor walls may consist of a ceramic. It is preferred that at least those parts of the reactor which are in contact with the reaction medium are coated with ceramic.

The preferred starting material of this process corresponds to the preferred starting material of the process described above. An acyl chloride of formula $R^1$—C(O)X is preferred wherein $R^1$ is $CF_3$, $CF_2H$, $CF_2Cl$, $C_2F_5$, $C_3F_7$. A vinyl ether of formula $CH_2$=C(H)—$OR^2$ is preferred wherein $R^2$ represents methyl, ethyl, n-propyl or isopropyl. The preferred precursor is CETFBO.

It has been found that alkenones, in particular ETFBO, and halogenated precursors, in particular CETFBO (1,1,1-trifluoro-4-chloro-4-ethoxybutan-2-one) can be advantageously be used as solvent for the reaction of the carboxylic acid halide with the vinyl ether according to the process of the present invention. The halogenated precursor and alkenone used as a solvent correspond to the halogenated precursor and its dehydrohalogenated alkenone, respectively.

In one embodiment, which is preferred, the liquid reaction medium for said reaction comprises an alkenone, in particular ETFBO, as a solvent. The alkenone is generally used in an amount of from 50 to 99% by weight, preferably from 60 to 99% by weight, more preferably from 75 to 99% by weight of the alkenone relative to the total weight of the reaction medium.

This embodiment is particularly advantageous for starting up said reaction.

The alkenone comprises preferably additional alkenone which is provided to the reaction from an external source, for example an earlier batch manufacture of alkenone. In one aspect of this embodiment, said reaction is carried out by introducing carboxylic acid halide into said alkenone containing liquid reaction medium, in particular during start-up of the manufacturing process. The formation of the halogenated precursor of the alkenone after introduction of a vinyl ether into the liquid reaction medium comprising the alkenone and the carboxylic acid halide will generally provide a liquid reaction medium containing the halogenated precursor and the alkenone.

It is understood that this embodiment may also be applied for reaction of the same type as reaction described above wherein the vinyl ether is not added to a reaction medium containing carboxylic acid halide, for example, vinyl ether may be dissolved in the alkenone containing reaction medium and carboxylic acid halide is then added to the reaction medium containing vinyl ether and alkenone.

In another embodiment, the liquid reaction medium for the reaction of the carboxylic acid halide with the vinyl ether comprises a halogenated precursor of the alkenone, in particular CETFBO. The halogenated precursor is generally used in an amount of from 50 to 99% by weight, preferably from 60 to 99% by weight, more preferably from 75 to 99% by weight of the halogenated precursor to the total weight of the reaction medium.

In a preferred aspect of this embodiment, the process is carried out in continuous mode. In a continuous process, the content of the halogenated precursor of the alkenone in the liquid reaction medium is generally kept in a range from 50 to 99%, preferably in a range from 60 to 99%, more preferably in a range from 75 to 99% by weight of halogenated precursor relative to the total weight of the reaction medium. This is particularly advantageous for a continuous process operated in steady-state, for example in a continuously stirred tank reactor (CSTR).

In a preferred aspect, the remainder of the liquid reaction medium comprises carboxylic acid halide.

The liquid reaction medium generally contains at least 0.5% by weight, preferably at least 1% by weight of carboxylic acid halide relative to the total weight of the reaction medium. Preferably this content is at least 5% weight. The liquid generally contains less than about 20% by weight of carboxylic acid halide relative to the total weight of the reaction medium. Preferably this content is less than 10% weight. Preferably, the liquid contains 5 to 10% by weight of carboxylic acid halide relative to the total weight of the reaction medium. This particular aspect may also be applied to the different embodiments of the process according to the invention described herein. The reaction can be carried out in the presence of an additional solvent. The term "additional solvent" is understood to denote a solvent different from the reactants, the products of said reaction and the additional alkenone or precursor of the alkenone. The solvent to be used may, for example, be an aromatic hydrocarbon such as benzene, toluene or xylene, an aliphatic hydrocarbon such as pentane or hexane; a halogenated hydrocarbon such as methylene chloride, chloroform or ethylene dichloride or fluorinated hydrocarbons such as 1,1,1,3,3-pentafluorobutane (commercialized by Solvay Fluor GmbH under the trademark Solkane® 365mfc); or an ether such as diethyl ether, dibutyl ether or tetrahydrofuran. Among them, an aromatic hydrocarbon is preferred. Particularly preferred among them, is benzene or toluene. These solvents may be used alone or in combination as a mixture. If appropriate, the solvent is used usually in an amount of from 1 to 35 parts by weight, preferably from 3 to 16 parts by weight, per part by weight of the carboxylic acid halide. It is however preferred to carry out the reaction in the substantial absence or absence of additional solvent.

In a particular embodiment, the solvent further comprises at least one haloether, for example a chloroether such as chloroalkyl-alkyl ethers, in particular chloroethyl-ethyl ether. In this case, the content of haloether in the liquid reaction medium is generally from 0.1 to 5% often from 0.5 to 2% by weight relative to the total weight of the liquid reaction medium. It has been found that haloethers are suitable solvents which can be incorporated in the liquid reaction medium, in particular in the indicated concentration ranges while achieving high productivity and selectivity to halogenated precursor of alkenone. In a continuous process, the content of haloether is preferably maintained in the concentration range indicated here above.

It is more particularly preferred to carry out the reaction in a liquid reaction medium consisting or consisting essentially of alkenone, halogenated precursor of alkenone, carboxylic acid halide and vinyl ether. This embodiment has particular advantages for subsequent process steps such as for example a thermolysis or purification operations.

In the process according to the invention and in the particular embodiments thereof, the molar ratio of acid halide to vinyl ether preferably is from 0.8 to 1.2, and particularly preferably from 0.8:1 to about 1. Most preferably, the molar ratio is about 1.

In the process according to the invention and in the particular embodiments thereof, the vinyl ether is generally introduced into the liquid reaction medium at a rate of from 0.01 to 2 mol/hour/mol of carboxylic acid halide. Preferably this rate is from 0.5 to 1.5 mol/hour/mol of carboxylic acid halide. A rate of about 1 mol/hour/mol of carboxylic acid halide has given good results.

The process according to the invention and the particular embodiments thereof can be carried out batchwise or continuously In the process according to the invention and in the particular embodiments thereof, it is especially beneficial, in particular in a continuous process to control the concentration of the vinyl ether in the liquid reaction medium. Generally, this concentration is less than 5% by weight relative to the total weight of the liquid reaction medium. Often the concentration of the vinyl ether in the liquid reaction medium is equal to less than 1% by weight relative to the total weight of the liquid reaction medium. Preferably, this concentration is equal to less than 0.5% by weight relative to the total weight of the liquid reaction medium. Generally, this concentration is at least 0.1% by weight relative to the total weight of the liquid reaction medium.

It has been found that controlling the concentration of the vinyl ether allows to avoid or control the formation of by products such as chloroethers or polymeric materials and improves the yield and purity of the alkenone which can be manufactured from the alkenone precursor produced according to the process of the present invention. The invention concerns in consequence also a process for the manufacture of a halogenated precursor of an alkenone, for example as disclosed here before, which comprises reacting a carboxylic acid halide continuously with a vinyl ether in a liquid reaction medium, wherein the concentration of the vinyl ether in the liquid reaction medium is controlled and preferably maintained in the ranges disclosed here before.

It has been found that use of the halogenated precursor of the alkenone and, preferably, the alkenone as solvents avoids particularly the formation of other unwanted compounds and improves the yield and purity of the organic products, in particular the halogenated precursor of the alkenone and, preferably, the alkenone. That is, use of the halogenated precursor of the alkenone and, preferably, the alkenone as solvents avoids complex post-treatments, for example, distillation of solvents, purification of the by-products caused by solvents etc.

In one embodiment of the invention, the halogenated precursor of the alkenone which is obtained according to the process of the invention can be used as such. For example, it can be used as solvent, e.g. as solvent in a subsequently performed process according to the present invention.

In another embodiment of the invention, the halogenated precursor of the alkenone which is obtained in the process according to the present invention is dehydrohalogenated by the elimination of hydrogen halide to form the respective alkenone. Consequently, the invention further concerns a process for preparing an alkenone, which comprises (a) reacting a carboxylic acid halide with a vinyl ether to form a halogenated precursor of the alkenone in a liquid reaction medium containing an alkenone or a halogenated precursor thereof, and (b) eliminating hydrogen halide from said precursor to form the alkenone.

According to one alternative, the elimination of hydrogen halide is carried out simultaneously during the formation of the halogenated precursor of the alkenone, for example, in the presence of an acid scavenger and/or by thermally inducing the elimination of hydrogen halide. The acid scavenger to be used may, for example, be a nitrogen-containing heterocyclic compound such as pyridine, quinoline or picoline; or a tertiary base such as triethylamine, dimethylaniline, diethylaniline or 4-dimethylaminopyridine. Among them, pyridine, triethylamine, dimethylaniline, diethylaniline or 4-dimethylaminopyridine is preferred. Among them, pyridine is particularly preferred. These acid scavengers may be used alone or in combination as a mixture. If appropriate, the acid scavenger is used in an amount of less than 1 equivalent, preferably less than 0.8 equivalents per mol carboxylic acid halide.

If desired, an additional solvent may be present during the elimination of hydrogen halide. The term "additional solvent" has the same meaning as defined above.

In a first particular embodiment, the carboxylic acid halide is trifluoroacetyl chloride. Preferably, the trifluoroacetyl chloride is fed in liquid state into the reaction medium.

In a second particular embodiment, the carboxylic acid halide is Chlorodifluoroacetyl chloride.

In a third particular embodiment, the carboxylic acid halide is Difluoroacetyl chloride.

In a forth particular embodiment, the carboxylic acid halide is trifluoroacetyl fluoride.

In a fifth particular embodiment, the carboxylic acid halide is (trifluoroaceto)acetyl fluoride.

In a sixth particular embodiment, which is preferred, the process for the preparation of a halogenated precursor of an alkenone and the elimination of hydrogen halide is carried out in the substantial or complete absence of an acid scavenger especially when a carboxylic acid chloride as described herein before is used.

In a seventh particular embodiment, which is preferred, the preparation of the halogenated precursor of the alkenone and the elimination of hydrogen halide is carried out in the substantial or complete absence of additional solvent.

In a eighth particular embodiment, which is preferred, the preparation of the halogenated precursor of the alkenone and the elimination of hydrogen halide is preferably carried out in the substantial or complete absence of an acid scavenger and of additional solvent, as described here before. The sixth to eighth, in particular the eighth particular embodiment can be advantageously combined with any of the first to fifth particular embodiment.

In the sixth to eighth particular embodiments of the process according to the invention, "Substantial absence" typically denotes an optional content of equal to or less than 1% by weight, more particularly equal to or less than 0.5% by weight of acid scavenger and/or solvent relative to the total weight of the reaction medium. "Complete absence" in this context typically denotes a process wherein no voluntary addition of acid scavenger and/or solvent to the reaction medium has been carried out. Typically "complete absence" means that no acid scavenger and/or solvent can be detected in a GC of the reaction medium.

In particular the sixth to eighth particular embodiments of the process according to the invention allow for particularly efficient isolation of, if desired, the halogenated precursor of the alkenone and in particular the desired alkenone as reaction proceeds selectively and separation is facilitated by the limitation albeit substantial absence of components different from the starting material and the products of the reaction.

As mentioned above, a preferred embodiment of the invention concerns a process for preparing an alkenone, which comprises (a) reacting a carboxylic acid halide with a vinyl ether to form a halogenated precursor of the alkenone in a liquid reaction medium containing an alkenone or a halogenated precursor thereof, and (b) eliminating hydrogen halide from said precursor to form the alkenone.

This embodiment of the process according to the invention and the particular embodiments thereof, generally comprises carrying out the reaction of step (a) at a first temperature and carrying out step (b) at a second temperature higher than the first temperature.

The first temperature is generally less than 50° C., often less than 40° C., preferably equal to or less than 30° C. In one aspect, the temperature is preferably equal to or less than about −25° C. The first temperature is generally at least −50° C., often equal to or greater than −40° C., preferably equal to or greater than −30° C.

The second temperature is generally at least 50° C., often equal to or greater than 60° C., preferably equal to or greater than 70° C. The second temperature is generally less than 150° C., often less than 100° C., preferably equal to or less than about 80° C.

The process according to the invention and the particular embodiments thereof, generally comprises carrying out the reaction of step (a) at a first pressure and carrying out step (b) at a second pressure lower than the first pressure.

The first pressure is generally chosen to maintain the reaction medium in the liquid state. For example, if trifluoroacetyl chloride is used as acid halide, the first pressure is advantageously atmospheric pressure at a reaction temperature of equal to or less than about −25° C. The first pressure is advantageously a pressure equal to or greater than about 4, preferably about 5 bar abs to equal to or less than about 10 bar at a reaction temperature of from 20 to 30° C.

The second pressure is preferably chosen to allow for fractional distillation at least of the alkenone from the reaction medium. A typical second pressure is from 1 to about $10^{-3}$ bar abs.

In one embodiment of the process according to the invention and the particular embodiments thereof, which is advantageous when the process is carried out batch-wise, steps (a) and (b) are carried out in the same reaction zone, for example, a vessel surmounted by a distillation column.

In another embodiment of the process according to the invention and the particular embodiments thereof, which is advantageous when the process is carried out batch-wise or continuously, thereof step (a) is carried out in a first reaction zone and step (b) is carried out in a second reaction zone different from the first reaction zone.

The first reaction zone is often an optionally stirred tank reactor, preferably a continuously stirred tank reactor. The second reaction zone can be, for example, a distillation column.

In an ninth particular embodiment, which is preferred, the process according to the invention further comprises separating the alkenone produced in step (b) from hydrogen halide, unreacted carboxylic acid halide and unreacted halogenated precursor (and some traces of polymeric material) and optionally recycling carboxylic acid halide to step (a) and halogenated precursor to step (b).

A distillation, in particular a fractional distillation, is preferred as separation technique to separate the alkenone, in particular from the reaction mixture of step (b). Preferably, a part of the reaction medium is removed from the reactor of step a), carried in a loop and returned to the reactor of step a). In such a loop, it is possible to cool the circulated part of the reaction medium. This serves to keep the temperature of the reaction mixture in a desired range. Further, as will be described below, circulating continuously a part of the reaction mixture improves the mixing of the reaction medium; the resulting turbulent state of the reaction medium helps to avoid hot spots.

The process according to the invention and in the particular embodiments thereof, preferably comprises carrying out the reaction of step (a) according to this specific embodiment.

The elimination of hydrogen halide in step b) can be performed by warming up the reaction medium to a range as indicated above. A preferred embodiment of the invention relates to a process for preparing an alkenone, which comprises the following steps:
(a) providing the halogenated precursor of the alkenone by manufacture from a carboxylic acid halide and a vinyl ether in accordance with any of the processes disclosed herein before or a combination thereof
(b) eliminating the hydrogen halide from said precursor to form the alkenone by a thermolysis treatment selected from a flash thermolysis, a vacuum thermolysis and a thermolysis under stripping with an inert gas.

For the purpose of the present invention, the term "flash thermolysis" refers to a process wherein the liquid reaction medium is heated up in a short time. Typical heating times for flash thermolysis are less than 1 hour, in particular less than 30 min, preferably about 15 minutes. Generally, the heating time is greater than 1 s, often greater than 15 s.

In particular aspects of the process according to this embodiment, the flash thermolysis is conducted at a temperature ranging from −20° C. to 140° C. and a period of time ranging from 30 seconds to 1 hour, preferably at a temperature ranging from 0° C. to 130° C. and a period of time ranging from 30 seconds to 30 min, more preferably at a temperature ranging from 20° C. to 120° C. and a period of time ranging from 30 seconds to 20 min.

The thermolysis or flash thermolysis can be optionally carried out under stripping with an inert gas stream such as nitrogen gas, argon gas.

For the purpose of the present invention, the term "stripping" denotes in particular a physical separation process where one or more components, in particular HCl, are removed from the liquid reaction medium by a gas stream. The liquid and gas streams can have concurrent or counter-current flow directions.

If appropriate, the stripping is advantageously carried out with a nitrogen stream.

The process according to this embodiment, generally comprises carrying out the thermolysis at a temperature of −20° C. to 140° C., preferably from 60 to 130° C., for example at equal to or about 80° C. and more preferably at equal to or about 120° C.

The thermolysis or flash thermolysis may be carried out under vacuum. In that case, the vacuum is preferably from 100 to 600 mbar.

It is understood that the different processes and embodiments disclosed herein apply in most preferred way to the manufacture of chlorotrifluoroalkoxybutanone from alkyl-vinylether and trifluoroacetic acid halide, in particular from trifluoroacetyl chloride and ethyl vinyl ether and subsequent elimination to form trifluoroalkoxybutenone, in particular ETFBO.

It is understood that the different processes and embodiments disclosed herein apply in most preferred way to the manufacture of chlorodifluoroalkoxybutanone from alkyl-vinylether and difluoroacetic acid halide, in particular from difluoroacetyl chloride and ethyl vinyl ether and subsequent elimination to form difluoroalkoxybutenone, in particular EDFBO.

Furthermore, the invention also relates to a process for preparing an alkenones and also an apparatus for preparing halogenated precursors of an alkenones, for example using the above apparatus.

In such process, previously produced pure organic product, for example ETFBO, is circulated to start up and is cooled, optionally with the help of a cooling machine. When the respective target temperature is reached, the first reactant (for example TFAC) is first of all fed in gaseous or liquid form, before the first reactor, into the circuit (in particular turbulent circuit) and then the second reactant (for example EVE) is added in slight stoichiometric excess (for example, TFAC: EVE=1:1.01 mol). The level in the flask of the circulation means is kept constant by operating a membrane pump and discharging into the second means. In which, conversion of organic products' precursors to the organic products with the elimination of hydrogen halide, for example conversion of CETFBO into ETFBO with HCl elimination, either takes place by in batches (in particular thermolysis) once the receiver of the second means is full or by continuously feeding the organic products' precursors (e.g. CETFBO) stream from the circulation means into the second means, which is then under an optional slight vacuum. Precision distillation then takes place continuously or in batches in a further distillation column downstream.

The examples here after are intended to illustrate the invention without however limiting it.

The examples here after are intended to illustrate the invention without however limiting it.

In these examples and throughout this specification the abbreviations employed are defined as follows: TFAC is trifluoroacetylchloride, EVE is ethyl vinyl ether, CETFBO is 4-Chloro-4-Ethoxy-1,1,1-trifluoro-3-butan-2-one, ETFBO is Ethoxy-1,1,1-trifluoro-3-buten-2-one.

EXAMPLE 1

Two-Step Manufacture of
4-Ethoxy-1,1,1-trifluoro-3-buten-2-one

Step (a)

In a 100 ml three-necked flask surmounted by a dry-ice cooler, equipped with a Pt100 internal thermometer 66.24 g (0.5 mole) trifluoroacetylchloride was condensed in at $-30°$ C. 36.06 g (0.5 mole) of ethyl vinyl ether was added dropwise over 1 hour. After the addition, further 0.5 mole trifluoroacetylchloride was added. GC of a sample showed almost quantitative yield of 4-Chloro-4-Ethoxy-1,1,1-trifluoro-3-butan-2-one.

Step (b)

After the reaction of step (a) described above, the flask was warmed to room temperature and subjected to fractional distillation in vacuo. A first fraction (B.P. 59.3-66.4° C. at 47 mbar) contained a mixture of 4-Chloro-4-Ethoxy-1,1,1-trifluoro-3-butan-2-one and 4-Ethoxy-1,1,1-trifluoro-3-buten-2-one, which could be redistilled to provide further 4-Ethoxy-1,1,1-trifluoro-3-buten-2-one. A second fraction (B.P. 66.4-70° C. at 30 mbar) contained pure Ethoxy-1,1,1-trifluoro-3-buten-2-one (E/Z ratio 98.5:1.5). The isolated yield was 97.5% of theoretical yield.

EXAMPLE 2

Manufacture of 4-Chloro-4-Ethoxy-1,1,1-trifluoro-3-butane-2-one and 4-Ethoxy-1,1,1-trifluoro-3-butene-2-one Under Turbulent Conditions and ETFBO as Solvent General procedure: Pure ETFBO, obtained by a previous synthesis, was placed into the flow part of a recirculation system and cooled using a chiller. This recirculation system comprises a 20 L flask, 2 one meter distillation columns filled with 10 mm glass Raschig rings placed on top of another distillation column, a circulation pump (1500 l/h), 3 tube reactors each with 3 m path length (diameter 1.5 cm). Once the desired temperature was reached in the recirculation system, gaseous or liquid trifluoroacetylchloride (15 kg/h; 113.2 mol/h) was introduced in the turbulent circulation in front of the first 3 m reactor and then a small molar excess of ethyl vinyl ether (TFAC/EVE=1:1.01) was added after the first 3 m reactor. The level in the 20 L flask of the recycle apparatus was kept constant by pumping material using a membrane pump into a second apparatus. This second apparatus which serves for the thermolysis of 4-Chloro-4-Ethoxy-1,1,1-trifluoro-3-butan-2-one (CETFBO) to 4-Ethoxy-1,1,1-trifluoro-3-buten-2-one (ETFBO), comprises a 100 L Pfaudler ceramic vessel with 3 one meter distillation columns filled with 10 mm glass Raschig rings and a cooler with removal. The conversion of CETFBO to ETFBO under loss of HCl takes place either through batchwise thermolysis when the ceramic vessel is full or through continuous feeding of the CETFBO stream from the recycle apparatus. The fine distillation was further carried out continuously or batchwise in the distillation columns.

EXAMPLE 2a

The recirculation system was filled with pure ETFBO and cooled to a temperature of 10° C. Following the general procedure, TFAC and EVE were introduced at a rate of 12.4 mol/h and 12.8 mol/h, respectively. A GC sample taken every hour at the top of the recycle apparatus, showed a complete reaction from TFAC with EVE whereby the CETFBO concentration was increasing continuously with a decreasing of the ETFBO concentration. The continuous introduction of TFAC and EVE was carried out during 8 hours and all the material was collected in the ceramic vessel. The thermolysis was carried out at 80° C. under a nitrogen stream, followed by a fractional distillation to provide 4-Ethoxy-1,1,1-trifluoro-3-buten-2-one in an isolated yield of 87% of the theoretical yield and with a purity (cis+trans isomer) of 98%.

EXAMPLE 2b

The same procedure was followed as example 2a but the recirculation system was kept at a temperature of 20° C. Ethoxy-1,1,1-trifluoro-3-buten-2-one was obtained in an isolated yield of 87% of the theoretical yield and with a purity (cis+trans isomer) of 98%.

EXAMPLE 3

Conversion of CETFBO to ETFBO by Thermolysis Treatment

General procedure: After the reaction of step (a), as described above in example 1, the flask, fitted with a reflux condenser, was heated to the desired temperature by using an oil bath. The thermolysis or flash thermolysis was performed under different conditions: at different temperatures, with or without an inert gas stream or under vacuum. The conversion of CETFBO to ETFBO was followed by GC analyses. When the composition of the reaction mixture remained constant, the resulting reaction mixture was further subjected to a distillation in vacuo (70° C., 20 mbar) to obtain Ethoxy-1,1,1-trifluoro-3-buten-2-one. The experimental data are summarized in Table 1. The thermolysis time refers to the time after which the composition of the reaction mixture remained constant.

TABLE 1

| Example | Conditions | Thermolyis time [min] | % wt of CETFBO | % wt of ETFBO (cis/trans) | Isolated yield of ETFBO (%) |
|---|---|---|---|---|---|
| 3a | 80° C. | 43 | 5.2 | 88.9/1.3 | 85.7 |
| 3b | 80° C./N$_2$ stream (24 l/h) | 80 | 0.3 | 97.6/1.6 | 91.5 |
| 3c | 80° C./vacuum (400 mbar) | 80 | 1.4 | 95.1/1.7 | 89.3 |
| 3d | 120° C. | 17 | 1.2 | 94.3/1.4 | 89.9 |

TABLE 1-continued

| Example | Conditions | Thermolyis time [min] | % wt of CETFBO | % wt of ETFBO (cis/trans) | Isolated yield of ETFBO (%) |
|---|---|---|---|---|---|
| 3e | flash thermolysis 120° C. | 13 | 1.0 | 94.9/1.5 | 93.0 |
| 3f | flash thermolysis 100° C. | 25 | 2.8 | 93.7/1.4 | 93.7 |

The % wt of CETFBO and % wt of ETFBO (cis/trans) were measured by GC analyses.

EXAMPLE 4

Reaction

1$^{st}$ Stage: Production of
4-chloro-4-ethoxy-1,1,1-trifluorobutane-2-on
(CETFBO)

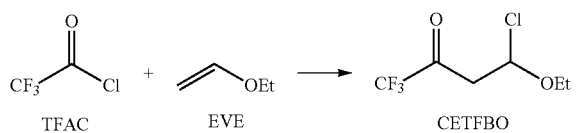

2$^{nd}$ Stage: Production of
4-ethoxy-1,1,1-trifluoro-3-butene-2-on (ETFBO)

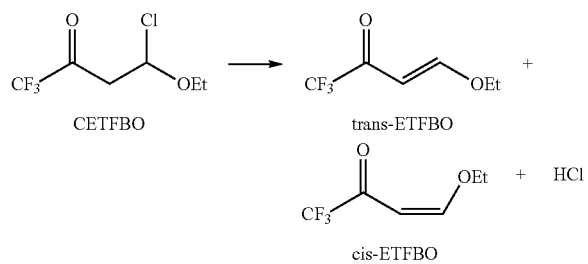

Charge:

| ETFBO | 0.700 mol | 119 g | 76.9% by weight |
| TFAC | 0.175 mol | 23.3 g | 15.0% by weight |
| EVE | 0.175 mol | 12.6 g | 8.1% by weight |

119 g (0.7 mol) ETFBO were presented in a three-necked flask with dry-ice cooler and magnetic agitator and were cooled to 0° C. 23.3 g (0.175 mol) TFAC were then introduced from a pressure flask. TFAC dissolved very easily in ETFBO. Then 12.6 g (0.175 mol) EVE was added all at once. A first sample was taken (GC analysis, WLD detector) after 21 minutes. There were still 2 GC-% TFAC in the mixture. After 60 minutes all the TFAC was converted. Thermolysis was then carried out for 1 hour at 80° C., until no more HCl escaped and the batch was fractionally precision distilled in a vacuum at $10^{-3}$ mbar. The ETFBO yield thus isolated amounted to 97% and the purity was 99.5% (98.0% trans-isomer, 1.5% cis-isomer).

EXAMPLE 5

Pure ETFBO was poured into the circulation apparatus and the temperature was adjusted to +10° C. TFAC was then added at a rate of 12.4 mol/h and EVE at a rate of 12.8 mol/h. GC samples taken hourly from the bottom of the circulation apparatus indicated complete conversion of TFAC with EVE. The concentration of the circulating CETFBO rose continuously, while the ETFBO concentration decreased continuously. The apparatus was operated under these conditions for 8 hours and the material was collected in the second apparatus. Subsequent thermolysis at 80° C. in a nitrogen stream to eliminate the HCl, followed by fractional precision distillation produced ETFBO in an isolated yield of 87% of the theoretical and a purity (cis+trans isomer) of 98.0%.

EXAMPLE 6

The experiment was repeated as described in example 5 except that the temperature was +20° C. The selectivity and isolated yield were comparable with the experiment at +10° C.

The invention claimed is:

1. A process for preparing a halogenated precursor of an alkenone, which comprises reacting a carboxylic acid halide with a vinyl ether in a liquid reaction medium, wherein the carboxylic acid halide is trifluoroacetyl chloride which is introduced into the reaction medium in liquid form, wherein the reaction is carried out under conditions of pressure and temperature under which said carboxylic acid halide is gaseous, and wherein, when the liquid carboxylic acid halide gets into the gaseous state in the liquid reaction medium, gas bubbles are generated to provide the reaction medium in turbulent state.

2. A process for the manufacture of a halogenated precursor of an alkenone which comprises reacting a carboxylic acid halide with a vinyl ether in a liquid reaction medium, wherein at least a part of the carboxylic acid halide is introduced into the reaction medium in liquid state, wherein the reaction is carried out under conditions of pressure and temperature under which said carboxylic acid halide is gaseous, and wherein, when the liquid carboxylic acid halide gets into the gaseous state in the liquid reaction medium, gas bubbles are generated in the liquid reaction medium to provide the reaction medium in turbulent state.

3. The process according to claim 2, for preparation of the halogenated precursor of the alkenone corresponding to Formula (I): R1-C(O)—CH2-CH(X)—OR2 (I) wherein X represents fluorine, chlorine or bromine and R1 represents a C1-C10 alkyl group which is optionally substituted by at least one halogen atom or R1 represents CF3C(O)CH2; and R2 represents aryl, substituted aryl, or a C1-C10 alkyl group which is optionally substituted by at least one halogen atom wherein an acid halide corresponding to Formula (II): R1-C(O)X (II) in which X and R1 has the meaning given above, is reacted with a vinyl ether corresponding to Formula (III): CH2=C(H)—OR2 (III) in which R2 has the meaning given above.

4. The process according to claim 3, wherein R2 is a C1-C4 alkyl group.

5. The process according to claim 3, wherein R1 is a fluorinated C1-C4 alkyl group.

6. The process according to claim 1, wherein the preparation of the halogenated precursor of an alkenone is carried out in the substantial absence of an acid scavenger.

7. The process according to claim 1, wherein the turbulent state is further achieved by an operation selected from the group consisting of a stirring and passing the reaction medium through a flow resistance.

8. The process according to claim 1, wherein the vinyl ether and the carboxylic acid halide are introduced into the liquid reaction medium through a concentric nozzle having an internal supply tube and an external supply tube, wherein the vinyl ether is supplied through the internal supply tube and the carboxylic acid halide is supplied through the external supply tube.

9. The process according to claim 1, wherein the process is carried out continuously.

10. The process according to claim 1, wherein the turbulent state is sufficient to avoid formation of hot spots.

11. The process according to claim 1, wherein the liquid reaction medium contains from 1% to less than about 20% by weight of said carboxylic acid halide.

12. The process according to claim 1, wherein the vinyl ether is introduced into the liquid reaction medium at a rate of from 0.01 to 2 mol/hour/mol of said carboxylic acid halide.

13. The process according to claim 1, wherein the reaction is carried out at a temperature from 0° C. to 40° C.

14. The process according to claim 1, wherein the reaction is carried out in a continuously stirred tank reactor.

15. The process according to claim 1, further comprising withdrawing at least a part of the liquid reaction medium and further reacting said part in a plug flow reactor.

16. A process for preparing an alkenone, which comprises (a) reacting a carboxylic acid halide with a vinyl ether to form a halogenated precursor of the alkenone according to claim 1, and (b) eliminating hydrogen halide from said precursor to form the alkenone.

17. The process according to claim 5, wherein R1 is a CF3 group.

18. The process according to claim 11, wherein the liquid reaction medium contains from 5% to less than about 20% by weight of carboxylic acid halide.

19. The process according to claim 14, wherein the reaction is carried out in a continuously stirred tank reactor with ceramic lining.

* * * * *